United States Patent [19]
Heyman et al.

[11] Patent Number: 5,637,799
[45] Date of Patent: Jun. 10, 1997

[54] METHOD AND APPARATUS FOR EVALUATING MULTILAYER OBJECTS FOR IMPERFECTIONS

[75] Inventors: Joseph S. Heyman, Williamsburg; Nurul Abedin; Kuen J. Sun, both of Yorktown, all of Va.

[73] Assignee: The United States of America as represented by the Administrator of the National Aeronautics and Space Administration, Washington, D.C.

[21] Appl. No.: 571,687

[22] Filed: Dec. 13, 1995

Related U.S. Application Data

[63] Continuation of Ser. No. 873,407, Apr. 15, 1992, abandoned.

[51] Int. Cl.$^6$ .................................................. G01N 29/04
[52] U.S. Cl. ............................ 73/600; 73/598; 73/602; 73/627
[58] Field of Search .......................... 73/598, 600, 582, 73/602, 627, 628, 599; 364/550, 552, 551.01

[56] References Cited

U.S. PATENT DOCUMENTS

| | | | |
|---|---|---|---|
| 3,576,126 | 4/1971 | Weighart | 73/614 |
| 3,592,050 | 7/1971 | Nutt, Jr. et al. | 73/588 |
| 3,623,358 | 11/1971 | Sugimoto | 73/588 |
| 3,813,926 | 6/1974 | Stubbeman | 73/627 |
| 4,184,373 | 1/1980 | Evans et al. | 73/588 |
| 4,277,977 | 7/1981 | Lubitz et al. | 73/587 |
| 4,344,326 | 8/1982 | Kahn | 73/587 |
| 4,366,713 | 1/1983 | Gilmore et al. | 73/588 |
| 4,509,369 | 4/1985 | Kuljis et al. | 73/628 |
| 4,674,334 | 6/1987 | Chimenti et al. | 73/628 |
| 5,000,045 | 3/1991 | Secoy | 73/587 |
| 5,005,415 | 4/1991 | Holroyd | 73/587 |
| 5,408,882 | 4/1995 | McKinley et al. | 73/602 |

FOREIGN PATENT DOCUMENTS

| | | | |
|---|---|---|---|
| 302359 | 12/1988 | Japan | 73/627 |
| 1078318 | 3/1984 | U.S.S.R. | 73/582 |

OTHER PUBLICATIONS

M.N. Abedin, J.S. Heyman, K. J. Sun and F. R. Parker, "NDE of multilayer ceramic chip capacitors based on acoustic waveguides excitation," *IEEE* Ultrasonics Symposium, 1990, pp. 1091–1094.

K. J. Sun and W. P. Winfree, "Propagation of acoustic waves in a copper wire embedded in a curing epoxy", *IEEE* Ultrasonics Symposium, 1987, pp. 439–442.

*Primary Examiner*—Hezron E. Williams
*Assistant Examiner*—Nashmiya Ashraf
*Attorney, Agent, or Firm*—Robin W. Edwards

[57] ABSTRACT

A multilayer object having multiple layers arranged in a stacking direction is evaluated for imperfections such as voids, delaminations and microcracks. First, an acoustic wave is transmitted into the object in the stacking direction via an appropriate transducer/waveguide combination. The wave propagates through the multilayer object and is received by another transducer/waveguide combination preferably located on the same surface as the transmitting combination. The received acoustic wave is correlated with the presence or absence of imperfections by, e.g., generating pulse echo signals indicative of the received acoustic wave, wherein the successive signals form distinct groups over time. The respective peak amplitudes of each group are sampled and curve fit to an exponential curve, wherein a substantial fit of approximately 80–90% indicates an absence of imperfections and a significant deviation indicates the presence of imperfections. Alternatively, the time interval between distinct groups can be measured, wherein equal intervals indicate the absence of imperfections and unequal intervals indicate the presence of imperfections.

20 Claims, 4 Drawing Sheets

METHOD AND APPARATUS FOR EVALUATING MULTILAYER OBJECTS FOR IMPERFECTIONS

This is a continuation of application Ser. No. 07/873,407 filed on Apr. 15, 1992, now abandoned.

ORIGIN OF THE INVENTION

The invention described herein was jointly made by employees of the United States Government and contract employees during the performance of work under a NASA Contract. In accordance with 35 U.S.C. 202, the contractors elected not to retain title.

BACKGROUND OF THE INVENTION

1. Technical Field of the Invention

The present invention relates generally to nondestructive evaluation of imperfections in ceramics and more particularly to an acoustic waveguide technique for detecting delaminations, voids and microcracks.

2. Discussion of the Related Art

At present, there is a need to develop improved technology for mounting very high speed electronic components in order to design circuits more precisely. That need has been partially fulfilled by the advent of surface mount chip capacitors. The presence of critical defects can cause premature failure. These defects can develop in the individual engineering components under normal operating conditions. Numerous inspection techniques have been developed for the detection of small and embedded defects that provide information about the integrity of the electronic materials. Nondestructive techniques are used to inspect the quality of production at the early stage of manufacture. The first stage of inspection is visual, and is suited only for relatively large external defects. This visual inspection can be enhanced by using microscopes to detect small and embedded defects.

A number of nondestructive inspection systems are being considered for inspecting multilayer ceramic capacitors (MLCC). The various testing methods used to investigate the MLCC are acoustic emission, X-ray radiography, neutron radiography, and acoustic microscopy. These techniques each possess disadvantages. Acoustic emission requires a large load to obtain good sensitivity which might cause flaws in the sample. X-ray or neutron radiography is unable to detect the small cracks in the sample. Acoustic microscopy is very expensive and difficult to use outside the laboratory.

U.S. Pat. No. 4,344,326 to Kahn describes a technique for testing of laminated capacitors using acoustic emission. The use of acoustic emission is based upon the premise that defects such as cracks and delaminations will propagate with the release of acoustic energy when an external stress is applied to a defective capacitor. In this technique, a capacitor is placed on a planar base and a ram applies a force in a direction perpendicular to the laminations of the capacitor. Any acoustic energy signals emanating from the capacitor under test will be transmitted through the ram, detected by an attached transducer and forwarded to an acoustic emission processor. The acoustic energy emitted by the application of the load can be detected, quantified and used as an indication of the presence and the severity of the physical defects.

An acoustic waveguide technique has been employed to observe the sensitivity of the acoustic amplitude of a propagated wave to the epoxy state and temperature of an epoxy. The wave is propagated through a copper wire embedded in the epoxy. The use of an acoustic waveguide is promising because it does not need any electrical contacts. This technique is described in "Propagation of Acoustic Waves in a Copper Wire Embedded in a Curing Epoxy," K. J. Sun and W. P. Winfree, *Proceedings of IEEE Ultrasonics Symposium*, pp. 439–442, 1987.

It is accordingly an object of the present invention to detect imperfections such as delaminations, voids and cracks in ceramics structure including multilayer ceramic chip capacitors.

It is another object of the present invention to accomplish the foregoing object nondestructively and noninvasively.

It is a further object of the present invention to achieve the foregoing objects using an acoustic waveguide technique.

Additional objects and advantages of the present invention are apparent from the drawings and specification which follow.

SUMMARY OF THE INVENTION

The foregoing and additional objects are obtained by a method and apparatus according to the present invention. A multilayer object comprising multiple layers arranged in a stacking direction is evaluated for imperfections such as voids, delaminations and microcracks. First, an acoustic wave is transmitted into the object in the stacking direction via an appropriate transducer/waveguide combination. The wave propagates through the multilayer object in a "W"-type path and is received by another transducer/waveguide combination preferably located on the same surface as the transmitting combination. The received acoustic wave is correlated with the presence or absence of imperfections by, e.g., generating pulse echo signals indicative of the received acoustic wave, wherein the successive signals form distinct groups over time. The respective peak amplitudes of each group are sampled and curve fit to an exponential curve, wherein a substantial fit on the order of 80–90% indicates an acceptable absence of imperfections and a significant deviation indicates the presence of imperfections. Alternatively, the time interval between distinct groups can be measured, wherein approximately equal intervals indicate the absence of imperfections and unequal intervals indicate the presence of imperfections.

DETAILED DESCRIPTION

Figure 1:
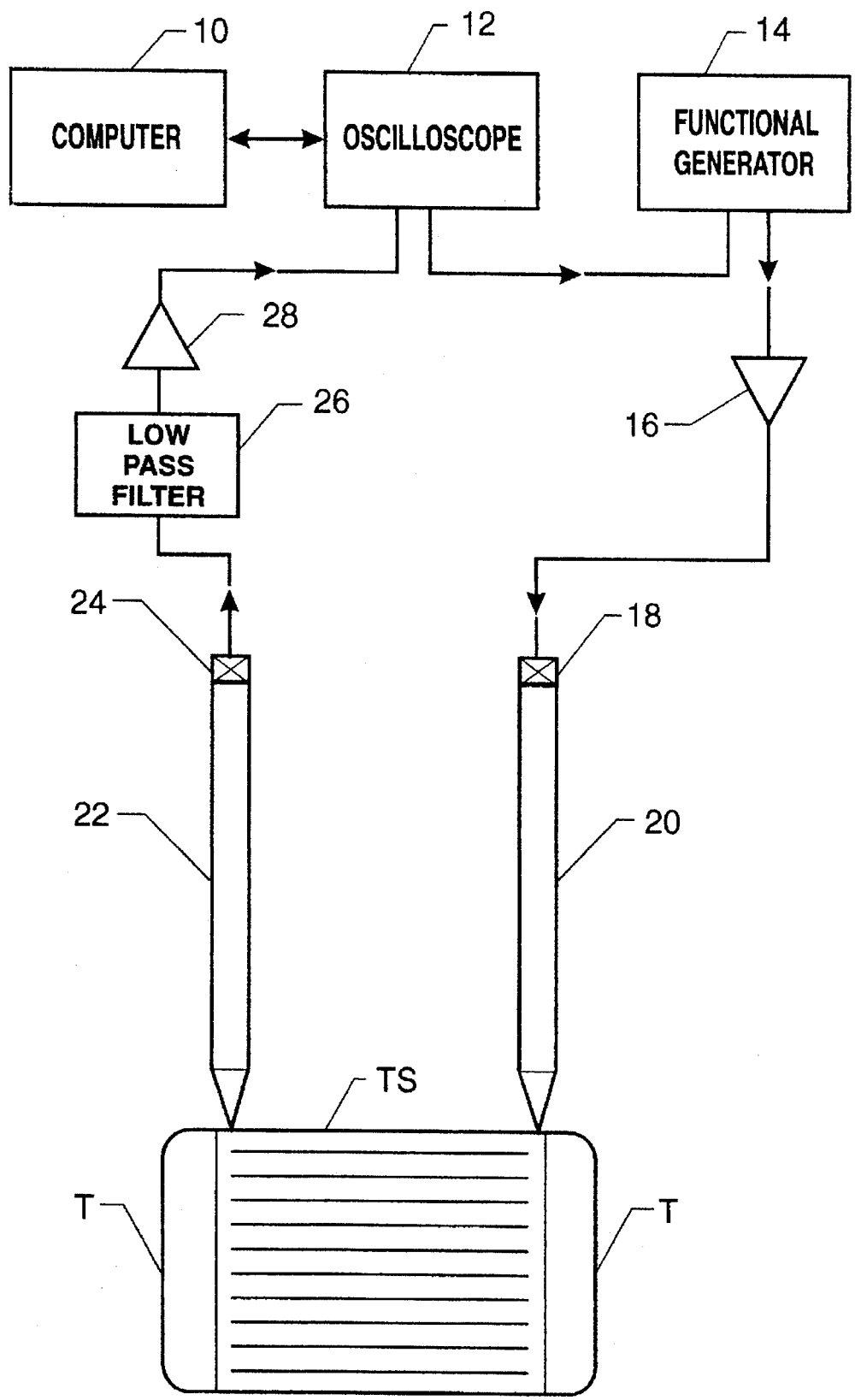
FIG. 1 is a schematic of an apparatus for evaluating a multilayer object for imperfections according to the present invention.

Referring to FIG. 1, a schematic diagram is shown of the apparatus used in the present invention. A computer 10 is provided which is connected to and controls an oscilloscope 12, preferably a digital oscilloscope such as the LeCroy 9400A which is commercially available from LeCroy Corporation. A line out from the oscilloscope is connected to a function generator 14 for generating a radio frequency (RF) pulse which is amplified by RF power amplifier 16. For example, the computer can command that a RF pulse with a center frequency of 1 MHz be generated. The frequency chosen is dependent upon the material properties and structural dimensions of the test specimen TS.

The amplified RF pulse is applied to the multilayer test specimen TS, which may be a multilayer ceramic chip capacitor (MLCC). The pulse is applied by a transmitting transducer 18 which is acoustically coupled to the TS via a first tapered buffer rod 20. Buffer rod 20 is uniformly cylindrical from a first end coupled to the transducer 18 throughout its body. The opposite end is tapered to a fine point in order to produce a sharp acoustic contact by reducing the interface area between this pointed end and the TS. The resulting acoustic wave propagates across the TS and is picked up by a second tapered buffer rod 22. Second tapered buffer rod 22 is similar in shape to first rod 20. By way of example, both rods may be copper and have an untapered diameter of approximately 700 µm.

A receiving transducer 24 is coupled to the untapered end of second buffer rod 22, detects the propagated acoustic wave, and converts it into an electrical signal which is transmitted to a low pass filter 26 and then amplified by amplifier 28. The amplified electrical signal is then supplied to the oscilloscope 12. Oscilloscope 12 permits a visual display of the received acoustic signal and transmits this data along with temporal data to the computer 10 as discussed in greater detail below with reference to FIGS. 2–5. This permits the evaluation of the MLCC, as discussed below.

Both the transmitting and receiving transducer/waveguide configurations are preferably on the same "top" or "bottom" surface of the multilayer test specimen, wherein the respective layers of the test specimen are stacked one atop the other from top to bottom. Accordingly, the propagated wave will travel through the layers in the stacking direction in a "V" or "W" pattern a significant number of times before being picked up by the receiving transducer/waveguide configuration, whereby an extensive survey of multilayer integrity can be performed as discussed below. The transmitting and receiving configuration can also be located on opposite sides of the TS so that the wave travels in a "N"-type pattern.

Table 1 summarizes results of oscilloscope readings of a test of a C-3216-CH-1H102K MLCC commercially available from TDK Corporation. The RF pulse was 1 MHz and amplitude readings were taken every 10 µs.

TABLE 1

| Amplitude (mV) | Time (t) (µs) |
|---|---|
| 8.84 | 96.6 ($t_0$) |
| 8.18 | 106.6 ($t_1$) |
| 7.21 | 116.6 ($t_2$) |
| 6.0 | 126.6 ($t_3$) |
| 5.31 | 136.6 ($t_4$) |
| 3.71 | 146.6 ($t_5$) |

TABLE 1-continued

| Amplitude (mV) | Time (t) (µs) |
|---|---|
| 2.68 | 156.6 ($t_6$) |
| 1.93 | 166.6 ($t_7$) |

Figure 2:
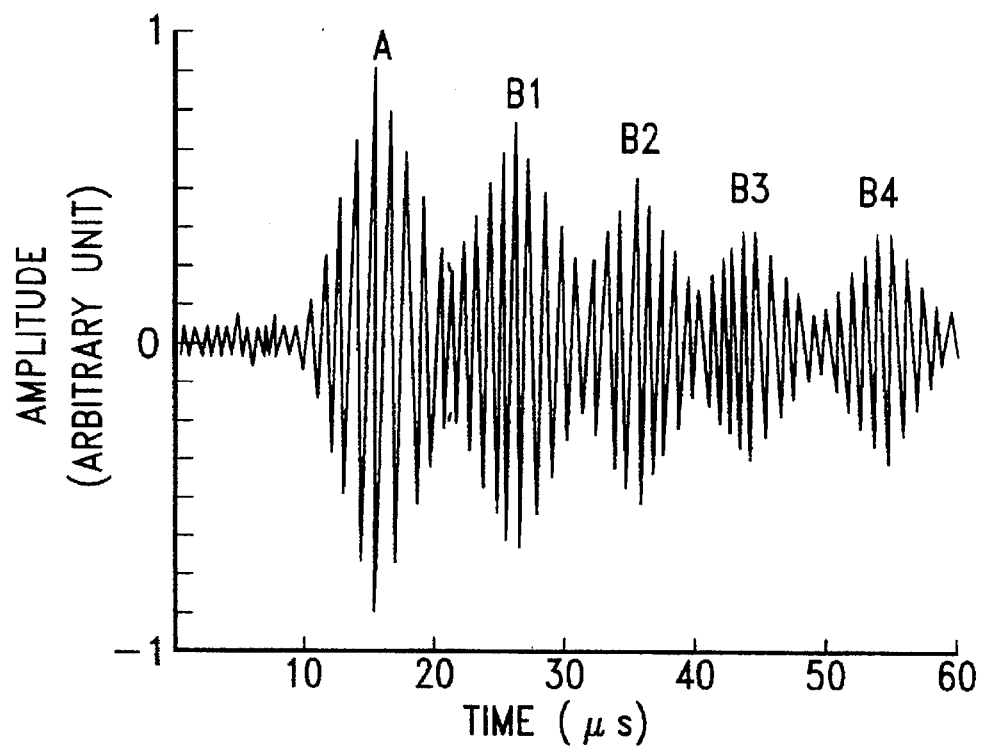
FIG. 2 is a graph of pulse echo signal groups taken over time for an undamaged multilayer chip capacitor.

The MLCC was determined to be relatively defect free prior to testing based on known manufacturing quality and microscopic inspection. FIG. 2 depicts pulse echo signals versus time for the same type of "good", i.e., relatively defect free, capacitor. The C-3216-CH-1H102K MLCC has typical dimensions of 3.2 mm×1.6 mm×0.85 mm. The buffer rod points were placed at the length ends so that the pulse traveled a typical length of 3.2 mm.

Both Table 1 and FIG. 2 clearly show a waveform consisting of an initial transmitted pulse (A in FIG. 2) followed by a series of undistorted echoes spaced at equal intervals ($B_i$ in FIG. 2) for a "good" MLCC. This information is digitally transmitted to the computer 10, where it is stored for subsequent analysis. Based on the time between subsequent echoes (approximately 10 µs) and the known path length (6.4 mm), the velocity of sound in the capacitor is determined by the computer or manually to be 640 m/sec.

Figure 3:
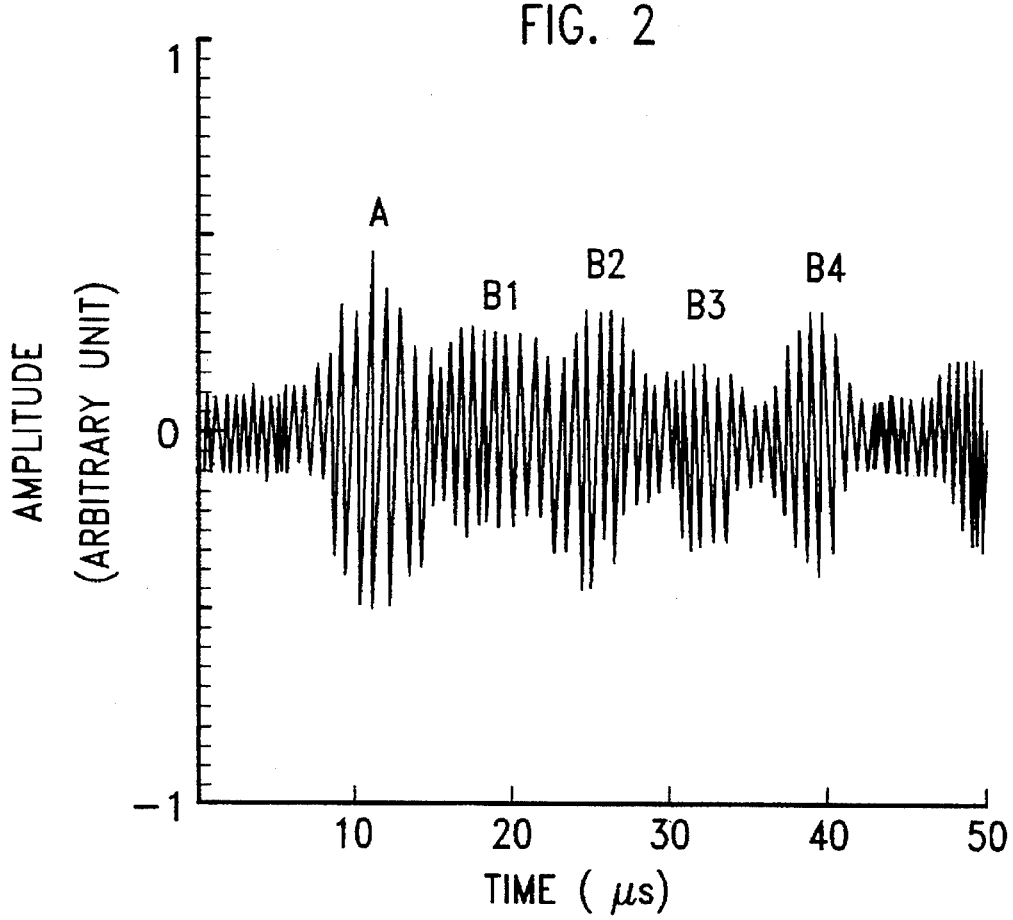
FIG. 3 is a graph of pulse signal groups taken over time for a damaged multilayer chip capacitor.

Next a damaged MLCC of the same type and manufacture was examined according to the present invention. The damage was caused by applying 1.7 kV of RF power across the terminal T in the acoustic propagation direction resulting in microcracks indicative of parametric or catastrophic failure. The microcracks were observed with a microscope. The damaged capacitor was then evaluated according to the method described above. FIG. 3 depicts the acoustic pulse echoes versus time for the damaged capacitor. Unlike the results of FIG. 2, FIG. 3 shows distorted echo trains which are unevenly spaced. Accordingly, the acoustic profile of a MLCC indicates the presence of damaging imperfections such as delaminations, voids, and microcracks. This acoustic profile can be evaluated as a function of time, i.e., computer sampled pulse groups or computer sampled peak amplitudes of each group which occur approximately periodically (equal intervals of time) indicates an acceptably undamaged MLCC whereas unequal intervals indicate an unacceptably damaged MLCC. Alternatively, the acoustic profile can be evaluated as discussed below in reference to FIGS. 4 and 5.

Figure 4:
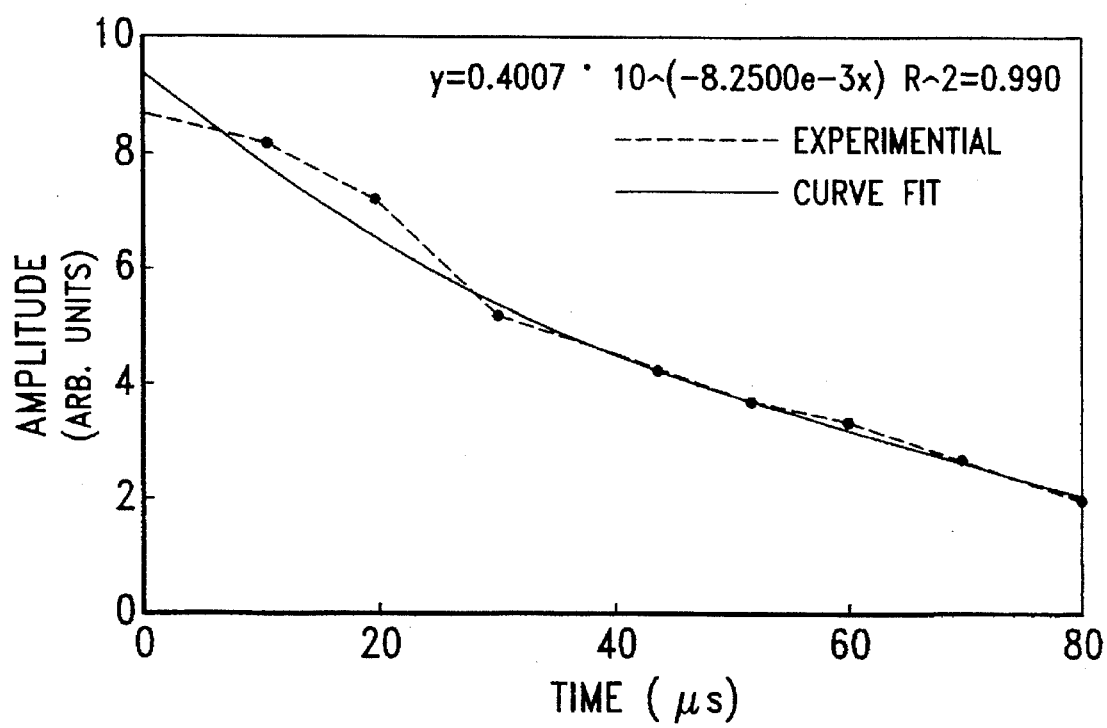
FIG. 4 is a graph of experimentally obtained peak amplitudes for each signal group in FIG. 2 and a model exponential curve.
Figure 5:
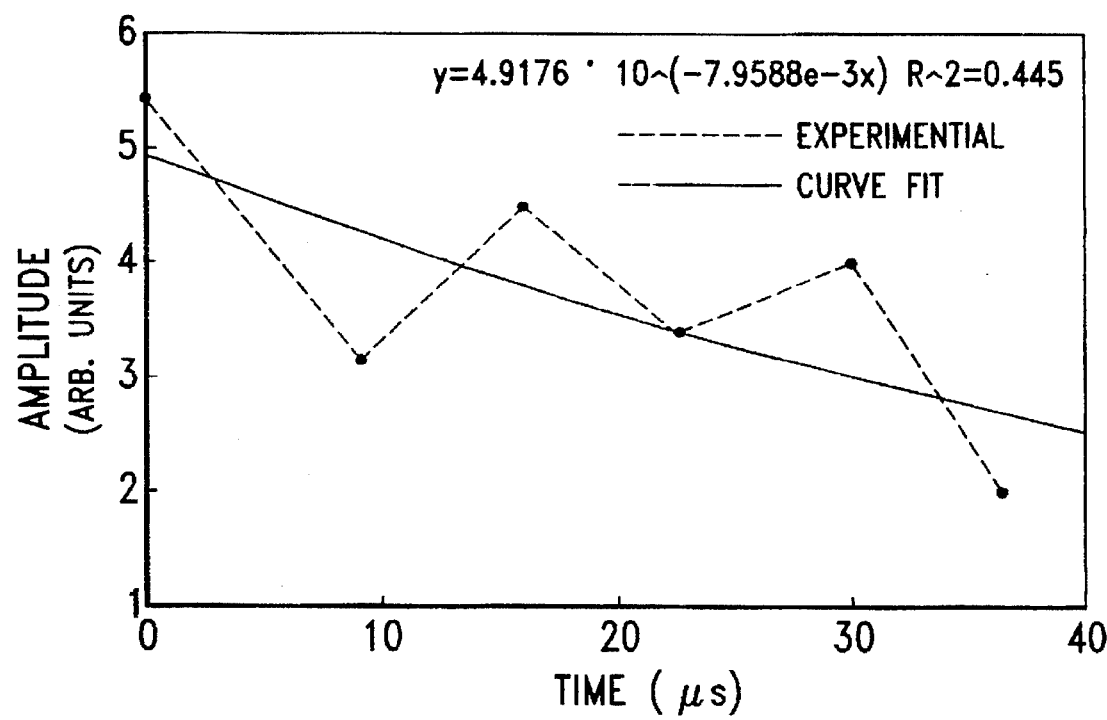
FIG. 5 is a graph of experimentally derived peak amplitudes for each signal group in FIG. 3 and a model exponential curve.

FIG. 4 shows the amplitude of the acoustic signal versus time for the undamaged "good" MLCC. Specifically, the peak amplitudes of each distinct wave envelope or group of FIG. 2 are sampled by the computer, plotted as a data point and connected to other data points via a dashed line. A model exponential curve fit, represented by a solid line, is applied to the experimental data curve via the computer executing a conventional curve fitting program. The data in this case closely follows the exponential curve fit. Thus, it is seen that the amplitude of the acoustic signal for the "good" MLCC decreases over time. Similarly, FIG. 5 depicts the experimental amplitude peaks versus time for the MLCC test results of FIG. 3 connected via a dashed line. Once again, a model exponential curve fit is applied to the data points. The experimental data clearly does not follow the exponential due to damage caused by the applied RF power. Accordingly, the presence of distorted wave trains and deviation of peak amplitude from an exponential curve fit indicates a damaged MLCC.

From the foregoing, it is clear that a substantial curve fit to the exponential indicates a relatively undamaged MLCC and a deviation from the curve fit indicates the converse. The percentage of fit indicative of a relatively undamaged state is of course application specific. A fit of at least approximately 80–90% has been found to be a good indication of an acceptable undamaged state and a deviation of more than approximately 10–20% to indicate an unacceptable damaged state.

Figure 6:
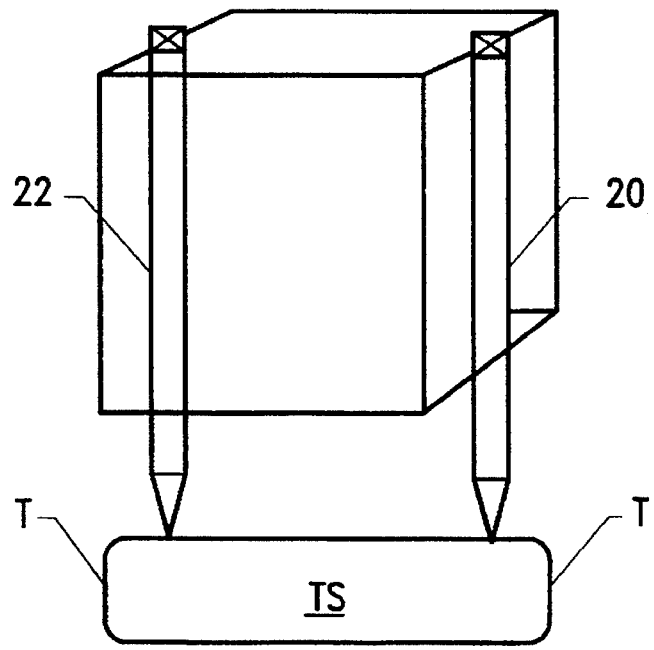
FIG. 6 is a perspective of an embodiment of a transducer/waveguide combination used in the present invention.

FIG. 6 shows the use of a spacing device 30 which maintains the physical, electrical, and acoustic separation of the tapered ends of the buffer rods 20 and 22 respectively coupled to transmitting and receiving transducers 18 and 24. Spacing device 30 is depicted as a box-like structure wherein the buffer rods are attached to perpendicular faces of the structure. The buffer rods should be spaced so as to contact the terminal ends T of the MLCC test specimen TS. Of course, various alternative holding devices could be employed, e.g., an adjustable spacer located between the buffer rods.

Figure 7:
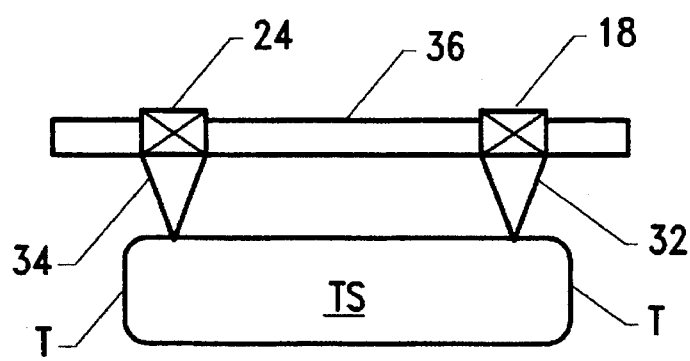
FIG. 7 is a side view of another embodiment of a transducer/waveguide combination.

FIG. 7 depicts an embodiment wherein the buffer rods are replaced with buffer cones 32 and 34. The transmitting and receiving transducers 18 and 24 are respectively coupled to the bases of cones 32 and 34.

Figure 8:
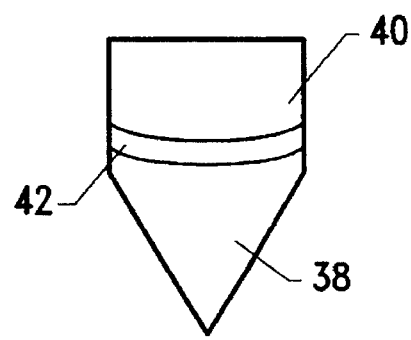
FIG. 8 is a side view of another embodiment of a transducer/waveguide combination.

In a preferred embodiment both the cone 38 and transducer 40 are fabricated from the same rod of a piezoelectric material, as shown in FIG. 8. Specifically, the rod is ground as shown and an electrode band 42 is bound around the ground object above the cone 38. The object is then placed in an electric field and raised above its Curie temperature $T_c$ to pole the electrode and create an active piezoelectric material between the electrode 42 and the opposite end of transducer 40. The cone 38 is inactive in a piezoelectric sense and continues to act as a waveguide with the same acoustic properties as the piezoelectric transducer.

The present invention is nondestructive and does require an acoustic couplant to perform an ultrasonic evaluation. Rather, a well spatially defined point source is used to transmit and receive ultrasonic waves. As demonstrated, the resulting pulse echo trains are indicative of the presence or absence of microcracks, delaminations and voids.

Many improvements, modifications and substitutions will be apparent to the skilled artisan without departing from the spirit and scope of the present invention as described herein and defined in the following claims.

We claim:

1. A method of evaluating a multilayer object for imperfections of voids, delaminations and microcracks, the multilayer object comprising multiple layers arranged in a stacking direction, the evaluation method comprising the steps of:

transmitting a pulsed acoustic wave into the multilayer object in the stacking direction;

receiving the transmitted acoustic wave, in the stacking direction, after the transmitted acoustic wave has propagated latterally through the multilayer object; and correlating the received acoustic wave with the presence or absence of imperfections in the multilayer object;

the correlating step further comprising:

generating echo signals indicative of the received acoustic wave; and curve fitting the echo signals to an exponential curve, wherein a significant curve fit to the exponential curve indicates an acceptable absence of imperfections in the multilayer object.

2. The method according to claim 1, wherein the acoustic wave is transmitted from a particular outer surface of the object and received at the same outer surface.

3. The method according to claim 1, wherein successive echo signals form distinct groups over time and further comprising sampling a respective peak amplitude of successive distinct echo signal groups, and wherein the sampled amplitudes are curve fit.

4. The method according to claim 1, wherein a curve fit of at least approximately 80–90% indicates an acceptable absence of imperfections in the multilayer object.

5. A method of evaluating a multilayer object for imperfections of voids, delaminations and microcracks, the multilayer object comprising multiple layers arranged in a stacking direction, the evaluation method comprising the steps of:

transmitting a pulsed acoustic wave into the multilayer object in the stacking direction;

receiving the transmitted acoustic wave, in the stacking direction, after the transmitted acoustic wave has propagated laterally through the multilayer object; and correlating the received acoustic wave with the presence or absence of imperfections in the multilayer object;

the correlating step further comprising:

generating echo signals indicative of the received acoustic wave; and curve fitting the echo signals to an exponential curve, wherein a significant deviation from the curve fit indicates an unacceptable presence of imperfections in the multilayer object.

6. The method according to claim 5, wherein successive echo signals form distinct groups over time and further comprising sampling a respective peak amplitude of successive distinct echo signal groups, and wherein the sampled peak amplitudes are curve fit.

7. The method according to claim 5, wherein a significant deviation from the curve fit of more than approximately 10–20% indicates an unacceptable presence of imperfections in the multilayer object.

8. The method according to claim 2, wherein said transmitting step comprises acoustically coupling a transmitting transducer to one end of a waveguide having an opposite pointed end, contacting the opposite pointed end to the particular outer surface of the multilayer object, and transmitting the acoustic wave from the transducer, through the waveguide, and into the multilayer object.

9. The method according to claim 2, wherein said receiving step comprises acoustically coupling a receiving transducer to one end of a waveguide having an opposite pointed end, contacting the opposite pointed end to the particular outer surface of the multilayer object, and receiving the transmitted acoustic wave with the receiving transducer via the waveguide.

10. An apparatus for evaluating a multilayer object for imperfections of voids, delaminations and microcracks, the multilayer object comprising multiple layers arranged in a stacking direction, the apparatus comprising:

means for transmitting an acoustic wave into the object in the stacking direction, such that the acoustic wave propagates laterally through the multilayer object;

means for receiving the transmitted acoustic wave after the transmitted acoustic wave has propagated laterally through the multilayer object; and means for correlating the received acoustic wave with the presence or absence of imperfections in the multilayer object;

the correlating means further comprising;

means for generating pulse echo signals indicative of the received acoustic wave; and means for curve fitting the echo signals to an exponential curve, wherein a significant curve fit to the exponential curve indicates the absence of imperfections in the multilayer object.

11. The apparatus according to claim 10, wherein a significant curve fit of at least approximately 80–90% indicates an acceptable absence of imperfections in the multilayer object.

12. The apparatus according to claim 10, wherein successive echo signals form distinct groups over time and further comprising means for sampling a respective peak amplitude of successive distinct echo signal groups, and wherein said curve fitting means curve fits the sampled peak amplitudes.

13. The apparatus according to claim 10, wherein said transmitting means transmits the acoustic wave from a particular outer surface of the object and said receiving means receives the transmitted wave at the particular outer surface.

14. The apparatus according to claim 10, wherein said transmitting means comprises a waveguide having a pointed end contacting the multilayer object, and a transmitting transducer coupled to the other end of the waveguide.

15. The apparatus according to claim 10, wherein said receiving means comprises a waveguide having a pointed end contacting the multilayer object, and a receiving transducer coupled to the other end of the waveguide.

16. The apparatus according to claim 14, wherein said receiving means comprises a waveguide of the receiving means having a pointed end contacting the multilayer object, and a receiving transducer coupled to the other end of the waveguide.

17. The apparatus according to claim 16, further comprises means for maintaining a desired spacing between the two waveguides.

18. An apparatus for evaluating a multilayer object for imperfections of voids, delaminations and microcracks, the multilayer object comprising multiple layers arranged in a stacking direction, the apparatus comprising:

means for transmitting an acoustic wave into the object in the stacking direction, such that the acoustic wave propagates laterally through the multilayer object;

means for receiving the transmitted acoustic wave after the transmitted acoustic wave has propagated laterally through the multilayer object; and means for correlating the received acoustic wave with the presence or absence of imperfections in the multilayer object;

the correlating means further comprising;

means for generating echo signals indicative of the received acoustic wave; and means for curve fitting the echo signals to an exponential curve, wherein a significant deviation indicates an unacceptable presence of imperfections in the multilayer object.

19. The apparatus according to claim 18, wherein successive echo signals form distinct groups over time and further comprising means for sampling a respective peak amplitude of successive distinct echo signal groups, and wherein said curve fitting means curve fits the sampled peak amplitudes.

20. The apparatus according to claim 18, wherein a deviation of more than approximately 10–20% indicates an unacceptable presence of imperfections in the multilayer object.

* * * * *